United States Patent
Feilkas et al.

(10) Patent No.: US 8,059,878 B2
(45) Date of Patent: Nov. 15, 2011

(54) REGISTERING MR PATIENT DATA ON THE BASIS OF GENERIC MODELS

(75) Inventors: Thomas Feilkas, Grafing (DE); Claus Schaffrath, München (DE)

(73) Assignee: Brainlab AG, Feldkirchen (DE)

(*) Notice: Subject to any disclaimer, the term of this patent is extended or adjusted under 35 U.S.C. 154(b) by 1127 days.

(21) Appl. No.: 11/838,300

(22) Filed: Aug. 14, 2007

(65) Prior Publication Data
US 2008/0039711 A1    Feb. 14, 2008

Related U.S. Application Data

(63) Continuation-in-part of application No. 10/811,330, filed on Mar. 26, 2004, now Pat. No. 7,787,932.

(60) Provisional application No. 60/822,706, filed on Aug. 17, 2006, provisional application No. 60/494,935, filed on Aug. 13, 2003.

(30) Foreign Application Priority Data

Mar. 26, 2003  (EP) .................................. 03006782
Aug. 14, 2006  (EP) .................................. 06016945

(51) Int. Cl.
    *G06K 9/00*    (2006.01)
(52) U.S. Cl. ....................................................... 382/131
(58) Field of Classification Search .......... 382/128–131; 128/920, 922, 923; 430/31, 39; 378/4, 21, 378/42, 44
See application file for complete search history.

(56) References Cited

U.S. PATENT DOCUMENTS

| 5,951,475 | A | * | 9/1999 | Gueziec et al. | ............... 600/425 |
| 6,563,941 | B1 | * | 5/2003 | O'Donnell et al. | ............ 382/131 |
| 6,711,433 | B1 | * | 3/2004 | Geiger et al. | ................. 600/431 |

(Continued)

FOREIGN PATENT DOCUMENTS

EP    1 348 394    10/2003

OTHER PUBLICATIONS

Fleute et al., "Nonrigid 3-D/2-D Registration of Images Using Statistical Models", Sep. 1999, Lecture Notes in Computer Science, pp. 138-147. Yao et al., "Assessing Accuracy Factors in Deformable 2D/3D Medical Image Registration Using a Statistical Pelvis Model", Oct. 2003, Proceedings of the Eight IEEE International Conference on Computer Vision.

*Primary Examiner* — Jason M Repko
*Assistant Examiner* — Shervin Nakhjavan
(74) *Attorney, Agent, or Firm* — Renner, Otto, Boisselle & Sklar, LLP

(57) ABSTRACT

A method for registering a non-patient-characteristic three-dimensional magnetic resonance data set (MR data set) to patient-characteristic data includes: producing or providing a non-patient-characteristic three-dimensional generic model of a body or body part containing body structure data; ascertaining or providing two-dimensional patient-characteristic detection data of a patient; using a transformation protocol for data-linking the body structure data of the three-dimensional generic model to the two-dimensional patient-characteristic detection data to change or adapt the generic model of the body or body part based on the ascertained two-dimensional patient-characteristic detection data, wherein the three-dimensional generic model is at least correlated with a three-dimensional MR reference data set; and changing or deforming at least a part of the three-dimensional MR reference data set by using the transformation protocol to generate a patient-characteristic three-dimensional MR data set that is registered to the fluoroscopic images.

24 Claims, 4 Drawing Sheets

U.S. PATENT DOCUMENTS

| | | | |
|---|---|---|---|
| 7,697,972 B2* | 4/2010 | Verard et al. | 600/424 |
| 2002/0052875 A1* | 5/2002 | Smith et al. | 707/10 |
| 2003/0130576 A1* | 7/2003 | Seeley et al. | 600/426 |
| 2004/0032261 A1* | 2/2004 | Schweikard et al. | 324/309 |
| 2004/0068187 A1* | 4/2004 | Krause et al. | 600/443 |
| 2005/0004443 A1* | 1/2005 | Okerlund et al. | 600/407 |
| 2005/0004451 A1* | 1/2005 | Vilsmeier et al. | 600/426 |
| 2005/0027193 A1* | 2/2005 | Mitschke et al. | 600/427 |
| 2005/0272991 A1* | 12/2005 | Xu et al. | 600/407 |
| 2006/0188139 A1* | 8/2006 | Khamene et al. | 382/130 |
| 2006/0234195 A1* | 10/2006 | Grund-Pedersen et al. | 434/262 |

* cited by examiner

REGISTERING MR PATIENT DATA ON THE BASIS OF GENERIC MODELS

RELATED APPLICATION DATA

This application claims priority of U.S. Provisional Application No. 60/822,706 filed on Aug. 17, 2006, which is incorporated herein by reference in its entirety, and is a continuation-in-part of U.S. application Ser. No. 10/811,330 filed on Mar. 26, 2004, now U.S. Pat. No. 7,787,932, which claims the priority of U.S. Provisional Application No. 60/494,935 filed on Aug. 13, 2003.

FIELD OF THE INVENTION

The present invention relates to a method and device for registering a non-patient-characteristic three-dimensional magnetic resonance (MR) data set to patient-characteristic image data, and more particularly, to at least two fluoroscopic images of the patient. Based on these image data, it is then possible to perform computer-assisted medical navigation.

BACKGROUND OF THE INVENTION

When examining a patient or preparing for surgery, in particular surgery in the region of bones such as, for example, spine, hip joint or knee operations, x-ray recordings or computer tomography (CT) recordings of the affected body structure are taken. From these recordings, the body structures can be clearly displayed. A drawback to such methods, however, is that x-ray radiation used to generate the images can be a burden to the patient's health.

Magnetic resonance or nuclear spin tomography recordings (MR recordings) can be produced without any burden to the health of a patient. Such imaging techniques are suitable for displaying soft tissue. Bone structures, however, generally are poorly identified or not identifiable in MR recordings.

In order to display both bone structures and soft tissues, it may be necessary to register or fuse CT recordings or x-ray recordings to MR recordings of a patient. This, however, can incur significant costs since computer tomographs and magnetic resonance tomographs are very expensive both to purchase, maintain and operate. Further, a plurality of CT recordings typically are produced, which can place a high radiation load on the patient.

Attempts have been made to develop systems that can be used without separately detected patient body structure data, for example on the basis of generic models of image data sets for body structures. However, such systems can lack the required accuracy for the patient to be treated in each case.

EP 1 348 394 relates to a method for computer-assisted, medical navigation in which the current position of a patient or part of a patient's body and the positions of medical treatment apparatus or treatment-assisting apparatus are detected by means of a position detection unit. The detected position data are assigned to body structure data in order to jointly use the body structure data and assigned position data within the framework of treatment assistance. Body structure data are used that are obtained on the basis of a three-dimensional generic model, wherein the model is adapted by data-linking on a two-dimensional plane with patient-characteristic, two-dimensional detection data.

These generic models, however, are not primarily based on MR data sets. Therefore, generic MR data cannot be correspondingly deformed and registered to the fluoroscopic images.

SUMMARY OF THE INVENTION

In a method for registering a non-patient-characteristic three-dimensional magnetic resonance (MR) data set to patient-characteristic image data, such as with image data of at least two fluoroscopic images of a patient, a three-dimensional generic or statistical model, in particular a surface model, of a body or body part is produced or provided. CT recordings, MR recordings, x-ray recordings or other images recorded by means of medical imaging systems, for example of average bodies or body parts, or of a particular group such as persons of a particular size or age, can be used to generate the generic or statistical model. These recordings can be stored in a database and retrieved in order to generate the generic or statistical model. Generic or statistical models that have already been produced and, for example, are based on body parts or body structures of a particular person sub-group also can be used. The generic or statistical models can be surface models of a body or body part.

Two-dimensional patient-characteristic detection data of a patient also can be ascertained, for example, by recording or providing at least two fluoroscopic images of the patient. The fluoroscopic images of the patient may have been recorded during previous examinations and/or surgery and stored in a database.

The non-patient-specific three-dimensional generic model, for example, maps the typical shape and/or structure of a body or body part and can be based on body parts or body structures of a plurality of persons and, thus, is not specific to a particular body or patient. The patient-specific fluoroscopic recordings contain patient-specific two-dimensional image data which are characteristic of a particular body or patient.

The generic model is adapted to the two-dimensional patient-specific fluoroscopic image data or patient-characteristic detection data. The image data or body structure data of the generic model can be adapted to the two-dimensional patient-characteristic detection data by means of a transformation protocol. In other words, the image data of the generic model can be deformed or changed in order to ensure an approximation of the three-dimensional generic model or of a two-dimensional projection of the generic model to the patient-specific detection data.

One way of adapting the generic model to the patient-specific detection data, such as the at least two patient-specific fluoroscopic image data sets, is described in the European patent application number 06012256, belonging to the Assignee of the present application, entitled "Shape reconstruction using x-ray images", the contents of which is hereby incorporated by reference in its entirety. According to EP 06012256, a general three-dimensional model of a structure is obtained, at least two two-dimensional images of the structure are obtained, and at least one image feature in the image is determined. The orientation of the general three-dimensional model of the structure with respect to the at least two two-dimensional images of the structure is determined such that the at least one image feature of a two-dimensional projection of the three-dimensional model matches the two-dimensional image feature or is very similar to it. Once the orientation of the three-dimensional model has been determined, the three-dimensional model is morphed or deformed in order to adapt the shape of the three-dimensional model to the at least two two-dimensional images.

In accordance with the methods, there is a correlation between the generic model and, for example, at least one generic, average or typical MR reference data set of a body or body part or body structure. The generic model preferably is at least based on the at least one MR reference data set and, in particular, also can be based on other reference data sets, such as CT reference data sets.

By adapting the generic model or the two-dimensional projection of the generic model onto the patient-specific fluoroscopic image data, a transformation protocol can be obtained, by means of which the body structure data of the generic model may be changed or deformed. At least a part of the three-dimensional MR reference data set can be deformed or changed by means of this transformation protocol. The MR reference data set thus can be adapted to the patient-specific or body-specific fluoroscopic image data. A patient-characteristic three-dimensional MR data set that is adapted to or registered to the fluoroscopic images thus can be generated or ascertained from the MR reference data set.

Both the at least partially adapted generic model and an at least partially patient-characteristic three-dimensional MR data set generated therefrom or corresponding thereto also can be linked to another patient-characteristic three-dimensional MR data set by a rigid transformation. This can enable navigation based on patient-characteristic three-dimensional MR data.

An advantage of the method is that when a generic or statistical model is used that has been adapted to the patient, it is no longer necessary, for a treatment in which medical navigation is to be provided, to produce a separate data set for the body structure. On the one hand, this spares the patient a high radiation load, for example from recording numerous x-ray or CT images, and on the other hand, the cost of producing such data sets can be minimized. Further, linking the generic body structure data with patient-characteristic detection data provides a data set that can be used to provide very accurate medical navigation. The generic model, which can be a universal model for the relevant body structure that includes all relevant data, does not from the outset comprise any data that are specifically tailored to the relevant patient. The generic model, however, once adapted with the aid of patient-characteristic detection data, does comprise sufficient anatomical or body structure data to provide a sufficiently accurate basis for medical navigation.

It is possible to work with the adapted image data set or model as with an image data set of the patient that is pre-operatively produced at significant cost and radiation load. For example, it is conceivable to use a generic model that comprises a typical or average body structure, for example a simple model representation of a vertebra, upper arm bone, lower arm bone, upper leg bone, lower leg bone or pelvic bone or other osseous body structure and/or soft tissue structure. The generic model also can comprise a statistical model of the body structure, in particular based on statistical evaluations of an indefinite number of image data sets, for example actual vertebra image data sets.

There also exists the possibility of directly providing the generic model as a kind of package of models for a plurality of body structures of the same type. In such a case, it is possible when adapting the model to select, from the plurality of models in the package, the one which best fits the patient-characteristic detection data, such that the model only need be slightly adapted (e.g., with computer assistance).

The generic model can comprise a two-dimensional or three-dimensional data set of a body structure, and in particular a geometric model. In other words, the generic model can be both three-dimensional data (for example, a vertebra model) and two-dimensional data (for example, virtual x-ray images) or also a model in the form of geometric data. These data, for example, can be angles and/or trajectory information that is displayed to the physician and indicates to the physician the ideal position of an implant.

The generic model can be correlated with at least one MR reference data set, such that changes or deformations of adaptations of the generic model by means of the transformation protocol can be applied analogously to the at least one MR reference data set. This enables the MR reference data set to be changed so as to generate an MR data set that is at least almost patient-characteristic.

The generic model also can be formed from at least one three-dimensional CT reference data set and the at least one three-dimensional MR reference data set. In this manner, the CT reference data set and the MR reference data set can so to speak form three-dimensional CT reference representations, CT reference models, MR reference representations and/or MR reference models corresponding to the generic model, wherein the corresponding CT and MR reference data sets preferably are registered to each other.

The generic or statistical model can be formed from a plurality of CT reference data sets and a plurality of corresponding MR data sets that are or can be registered to each other.

A plurality of CT reference data sets preferably are ascertained or provided in order to form the generic model. Also, MR reference data sets corresponding to the plurality of CT reference data sets preferably are ascertained or provided, and the MR reference data sets preferably are registered to their corresponding CT reference data sets. The generic model can be produced, for example, as a surface model from these data sets that are registered to each other, wherein a CT reference model can be produced from the plurality of CT reference data sets and an MR reference model can be produced from the plurality of MR reference data sets. These data sets can be correlated with the generic model or definitively assigned, or underlie the generic model.

If the generic model is deformed due to being adapted to the patient-specific image data or detection data, this deformation obeys a transformation protocol or mapping protocol. By deforming the generic model, a model that is adapted to the actual body structures of the patient can be produced. If the transformation protocol is applied to the MR reference data sets that are correlated with the generic model, or to the MR reference model, then an MR representation that is approximated to the body structures of the patient results. This establishes a relationship between the ascertained MR representation and the fluoroscopic images of the patient, such that the MR reference data that are approximated to the actual patient data or the adapted MR reference model can be registered to the fluoroscopic images. The transformation protocol also can be applied to the CT reference model in order to obtain a CT reference model that is adapted to the actual patient data.

In addition, the adapted generic model also can be registered to a corresponding patient-characteristic MR data set by means of a fixed registration or transformation. The adapted generic model thus can be additionally adapted or approximated to the actual patient structures, in particular the actual soft tissue structures. It is also possible to only register the adapted three-dimensional MR reference model to the patient-characteristic MR data set by means of a fixed registration, in order to obtain a more accurate or more patient-specific MR model.

It is also possible to produce or provide a plurality of CT reference data sets, from which the generic model is or can be generated. A CT reference data set, for example, can be selected as a CT main shape reference data set from the plurality of CT reference data sets. An MR main shape reference data set corresponding to this CT main shape reference data set can be produced or provided, wherein the CT main shape reference data set can be registered to the MR main shape reference data set.

The generic model thus can be generated exclusively from or by means of CT reference data sets, such that the generic model can be accurately and quickly adapted to the patient-specific fluoroscopic images. The generic model can be generated from the plurality of CT reference data sets, such as CT training reference data sets, and the CT main shape reference data set. One MR main shape reference data set preferably is registered to the CT main shape reference data set, wherein a correlation exists between the generic model and the MR main shape reference data set.

It is possible to produce a plurality of CT reference data sets of the thoracic vertebra of various persons, for example, such as two, three, four, five, six, seven, eight or more CT reference data sets. By way of example, six CT reference data sets of thoracic vertebrae of various persons can be read from a database or otherwise ascertained, wherein one of the six CT reference data sets preferably is selected as the CT main shape reference data set. An MR main shape reference data set that is registered to the CT main shape reference data set preferably also is read off from the database, or an MR main shape reference data set that corresponds to the CT main shape reference data set is produced and is registered to the CT main shape reference data set. Based on the other five CT reference data sets, the generic model, for example, can be ascertained only using the extracted surface information of the five CT reference data sets so as to produce a surface model as the generic model. One way of producing the generic model as a surface model is described in: M. Fleute and S. Lavalle, "Building a complete surface model from sparse data using statistical shape models: Application to computer-assisted knee surgery", in MICCAI, pages 878-887, 1998, which is incorporated by reference in its entirety.

By deforming at least a part of the generic model, the generic model can be adapted to the patient-specific fluoroscopic images by means of an adaptation protocol or transformation protocol, such as a three-dimensional transformation protocol. Such three-dimensional transformation protocol describes or specifies how a part of the generic model or the entire generic model has to be shifted or repositioned in order to achieve the greatest possible match between the generic model and the patient-specific image data.

This transformation protocol, for example, can be applied to the entire MR main shape reference data set to obtain from the MR reference data set an approximate patient-characteristic MR representation that is related to the fluoroscopic image data. The transformation protocol also can be analogously applied to the CT main shape reference data set, in order to transform or deform its image data.

The transformation protocol also can be applied to a part of the MR main shape reference data set that is registered to the CT main shape reference data set, or to a main shape reference data set formed from the CT main shape reference data set and the MR main shape reference data set. The transformation protocol preferably is only applied to the regions or structures of the main shape reference data set or MR main shape reference data set that can be definitively identified or referenced in the fluoroscopic image data and/or the generic model, such that an accurate or reliable transformation can be ensured with respect to these points. The structures, such as soft tissue structures, muscles or skin structures, that are not displayed in the fluoroscopic images and/or the generic model (e.g., the generic model generated from the CT data sets) can remain unchanged (e.g., they are not subjected to the transformation). An MR main shape reference data set that is registered to the CT main shape reference data set can be ascertained. Alternatively, a main shape reference data set that is formed from the CT main shape reference data set and the MR main shape reference data set can be generated. In the generated data sets, only the structures or parts that were significantly adapted or deformed are adapted to the patient-specific image data. The image data for which it is uncertain whether a deformation is necessary, such as image data that cannot be identified or displayed in the fluoroscopic images and/or the generic model, preferably remain unchanged.

The main shape reference data set approximated to the actual patient structures or the MR main shape reference data set can be improved or additionally adapted to the actual patient structures. This may be accomplished by registering the already adapted main shape reference data set or MR main shape reference data set to a corresponding patient-characteristic MR data set by means of a fixed registration or transformation. This enables the regions of the adapted MR main shape reference data set that initially remained unchanged to be filled in or changed.

This approach exhibits an array of advantages. Non-patient-specific CT data sets that are easy to ascertain or record can be used to produce the generic model. In this approach, only the main shape reference data set comprises an MR main shape reference data set and a CT main shape reference data set, which results in a significant reduction in labor and costs. Also, only the data of the main shape reference data set that also can be displayed in the fluoroscopic images and/or the generic model, and the patient-specific position of which can thus be correctly ascertained to a high probability, may be changed based on the ascertained transformation protocol. The fixed registration of the adapted main shape reference data set to the patient-specific MR data set also represents a simple, accurate and quick process.

Various types of patient-characteristic data that can be used to adapt the generic model are outlined below. Also, it is always possible to use combinations of such data, referred to below as diagnostic data.

The patient-characteristic data can be x-ray image data, such as from x-ray images produced beforehand or during the treatment, in particular bi-planar or multi-planar x-ray images. One example would be where x-ray images are already available for the patient that were produced within the framework of previous examinations. Data concerning body structures from these "old" x-ray images are particularly suitable if deviations in shape as compared to the generic model are to be factored in.

It is, however, also possible to produce individual x-ray images of the patient even during the treatment and to then incorporate this information into adapting the generic model. An advantage as compared to conventional "x-ray navigation" is that it is not necessary to produce a large number of x-ray images, as used in x-ray image based navigation. By contrast, it is sufficient to produce only one or very few x-ray images in order to adapt the generic model, which in addition can be limited to a very small portion of the body. This significantly reduces the radiation load as compared to conventional x-ray navigation.

The above also applies similarly to computer tomography or nuclear spin tomography image data. It is possible to use image data obtained from tomography detections produced much earlier, but the information of which is sufficient to suitably adapt the generic model.

It is not necessary, however, to use complicated patient-characteristic detection data or diagnostic data in this way to sufficiently adapt the generic model. It can be perfectly sufficient to use acquired point position information on the body structure of the patient, in particular natural or artificial landmarks. The patient-characteristic diagnostic data, for example, can be just the distance between two landmarks (for example bone extensions) which alone can provide sufficient information as to how the generic model is to be restructured. Data concerning the size, weight or body portion lengths or limb lengths of the patient can also be used as a basis for to adapt the generic model.

The generic model can be adapted by one or more of the following methods:
- manually adapting with the aid of image representation assistance, in particular by displacing points and landmarks or shifting, rotating, expanding or compressing the generic model on a screen output by means of a user interface;
- automatic image fusion methods that are in particular based on automatically identifying particular anatomical features;
- image data of the generic model, in particular digitally reconstructed x-ray images, and image data from computer tomography or nuclear spin tomography image data sets can be superimposed or fused together.

A deformation and/or rotation protocol can be used as the transformation protocol of the generic model.

The generic model thus can be fused with patient-specific information or image data either automatically, for example by automatically identifying particular anatomical features that are critical for fusing, or also manually, for example by shifting, rotating, and/or stretching/warping. If the generic model is fused with actual patient information with the aid of acquiring an indefinite number of items of point information on the patient (landmarks), it is possible to use a so-called surface matching method, e.g., a computer-assisted image adapting method, to fuse the image data. Detecting the diagnostic data and adapting the generic model from the various methods described above can be combined such that in addition to the diagnostic data (for example, intra-operatively acquired x-ray images), additional points on the patient also are recorded in the form of landmarks or randomly acquired points and used to accurately detect and adjust the position of the model or even its shape, so as to enhance navigation accuracy.

Generally speaking, the position data obtained by ascertaining the patient-characteristic detection data, in particular by acquiring landmark positions or by x-ray image recordings registered in a navigation system, can be used in the method to register the adapted body structure data in the navigation system and to graphically represent or use treatment apparatus or treatment-assisting apparatus registered to the adapted body structure. In other words, the step of detecting the diagnostic data can be simultaneously used to register the patient and the adapted generic model for navigation. As soon as the data of the model have been fused with registered data, e.g., data which have been definitively determined in their spatial position, for example registered fluoroscopic images of an x-ray navigation software, or as soon as the data of the model have been registered to landmarks, or a combination of both methods, they can be used for computer-assisted surgery and for minimally invasive operations, e.g., by displaying instruments or implants in relation to a fused model.

Also provided is a computer program which, when it is loaded onto a computer or is running on a computer, performs a method as described above, and to a program storage medium or computer program product comprising such program.

A device for registering a three-dimensional magnetic resonance (MR) data set to at least two fluoroscopic images of a patient comprises a data detection device, a navigation system for ascertaining the three-dimensional spatial position of the data detection device, and a computational unit such as a computer connected to the navigation system. Patient-specific detection data such as fluoroscopic images can be recorded by the data detection device, wherein the navigation system serves to ascertain the three-dimensional spatial position of the data detection device relative to the body structure to be recorded.

The computational unit preferably is connected via a wire connection or wirelessly to the navigation system. All the method steps described above that utilize computational operations can be performed or ascertained by the computational unit. The computational unit can ascertain a three-dimensional generic model, in particular a surface model, for bodies or body parts of various persons, wherein the generic model contains patient-specific body structure data. The three-dimensional generic model can contain or be based on at least one three-dimensional MR reference data set or can at least be correlated with the three-dimensional MR reference data set. The computational unit can change or deform or adapt the generic model based on the ascertained two-dimensional patient-characteristic detection data by means of a transformation protocol for data-linking the body structure data of the three-dimensional generic model to the two-dimensional patient-characteristic detection data. The computational unit can also change or adapt at least a part of the three-dimensional MR reference data set by means of the transformation protocol, in order to generate or ascertain a patient-characteristic three-dimensional MR data set which is registered to the fluoroscopic images.

BRIEF DESCRIPTION OF THE DRAWINGS

The forgoing and other features of the invention are hereinafter discussed with reference to the drawing.

DETAILED DESCRIPTION

Figure 1:
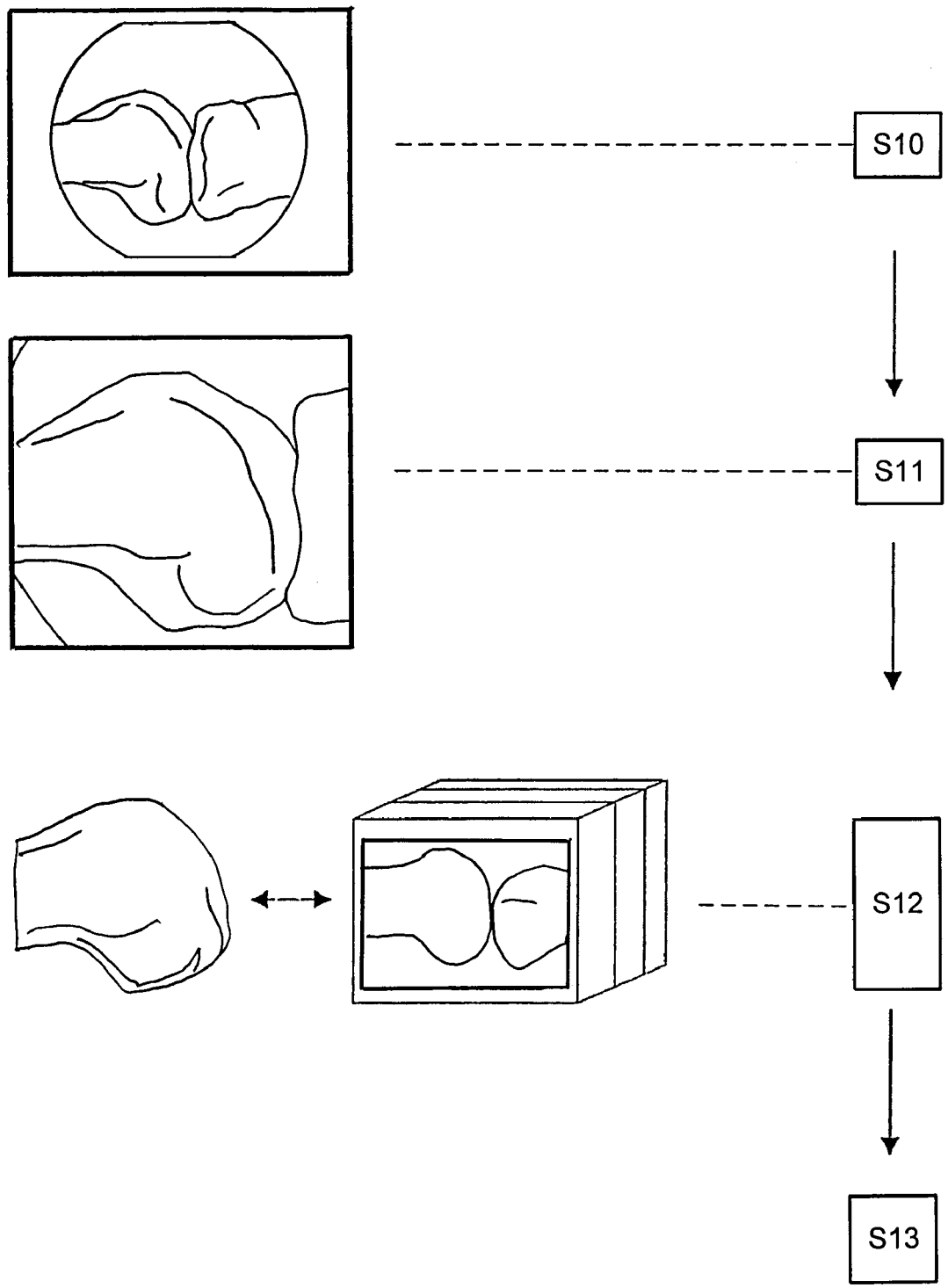
FIG. 1 is a flow diagram illustrating an exemplary method in accordance with the invention.

FIG. 1 is a flow diagram illustrating a first exemplary method for registering patient data on the basis of generic models. At least two fluoroscopic images of a body region of a patient are initially recorded in step S10. These fluoroscopic images contain patient-specific data such as patient-specific structures or shapes. A non-patient-specific adaptive generic model, which, for example, can include a plurality of data sets such as CT data sets, MR data sets, x-ray data sets or other data sets, is adapted to the fluoroscopic image data in step S11 by means of a transformation protocol. The transformation protocol at least partially adapts the initially non-patient-specific generic model to the actual patient-specific structures apparent from the fluoroscopic images. In the next step, step S12, the generic model, which has already been partially adapted, is registered with respect to a patient-specific MR data set, or conversely, the patient-specific MR data set is registered with respect to the generic model that has already been partially adapted. Preferably, a rigid registration that does not deform the generic model and, for example, can fill in previously indefinite structures or regions is used. An MR reference data set contained in the generic model is therefore also registered to the patient-specific image data. In a subsequent step, step S13, it is possible to navigate based on the fluoroscopic images, the generic model and the patient-specific MR data set.

Figure 2:
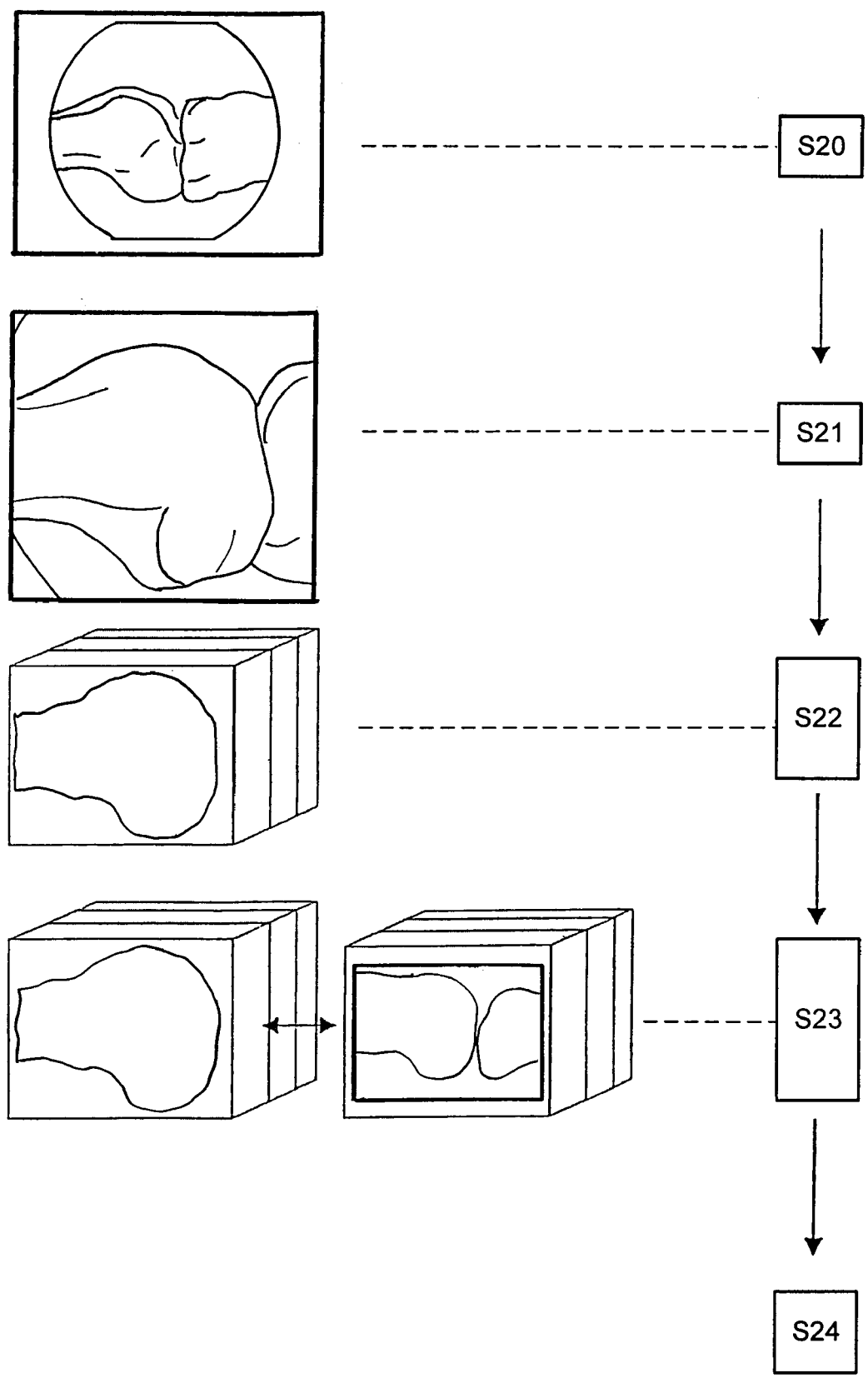
FIG. 2 is a flow diagram illustrating another exemplary method in accordance with the invention.

FIG. 2 is a flow diagram illustrating a second exemplary method for registering patient data on the basis of generic models. As explained in relation to FIG. 1, fluoroscopic images of a patient are produced in step S20. A non-body-specific generic model also is ascertained that is based on CT data sets of a plurality of individuals. This generic model is adapted to the fluoroscopic images in step S21 by means of a transformation, such that those regions of the generic model are deformed that are formed or shaped differently in the body-specific fluoroscopic images.

A transformation protocol is therefore ascertained in step S21 that describes the deformation of the non-body-specific generic model for adapting it to the body-specific image data. By means of this transformation protocol, an MR reference data set that is related to the generic model is deformed in step S22, wherein preferably only those regions of structures of the MR reference data set are deformed that are also formed or displayed in the generic model. It is possible to navigate based on the partially adapted MR reference data set alone.

Alternatively or additionally, the MR reference data set that has already been partially adapted is registered in step S23, preferably rigidly or fixedly, to an ascertained patient-specific MR data set. Alternatively, the patient-specific MR data set is registered, preferably rigidly, to the MR reference data set that has already been partially adapted. The data sets are registered such that while previously unchanged regions or regions of the MR reference data set that are different relative to the MR data set are filled in or changed, the MR reference data set is not however deformed. The MR reference data set is thus registered to the patient-specific data and to the fluoroscopic images. In a subsequent step, step 24, it is possible to navigate based on the fluoroscopic images, the generic model and the patient-specific MR data set.

Figure 3:
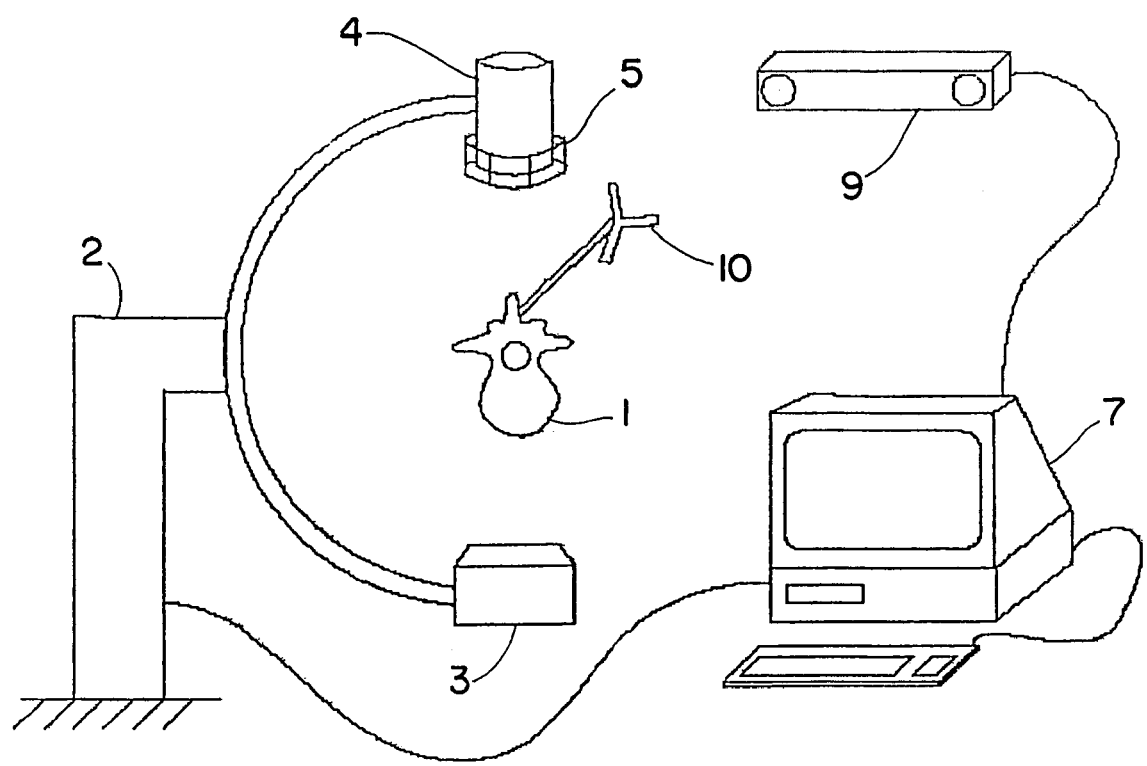
FIG. 3 illustrates an exemplary device for implementing the method in accordance with the invention.

FIG. 3 shows an embodiment of a device for implementing the methods described herein, comprising an x-ray device 2 formed as a C-arm, by means of which fluoroscopic images of a patient on whom a reference star 10 is preferably arranged can be recorded (such as recordings of the thoracic vertebra 1 of a patient). The x-ray device comprises a radiation source 3, an image amplifier 4 and an x-ray screen or x-ray equipment 5, by means of which registered fluoroscopic images can be produced. The device also comprises a navigation system 9, by means of which the position of the x-ray device 2 with respect to the patient can be ascertained by detecting the reference star 10 arranged on the patient. The navigation system 9 is connected to a computer 7 which comprises a memory or database and can perform computational operations needed to perform the method in accordance with the invention.

Figure 4:
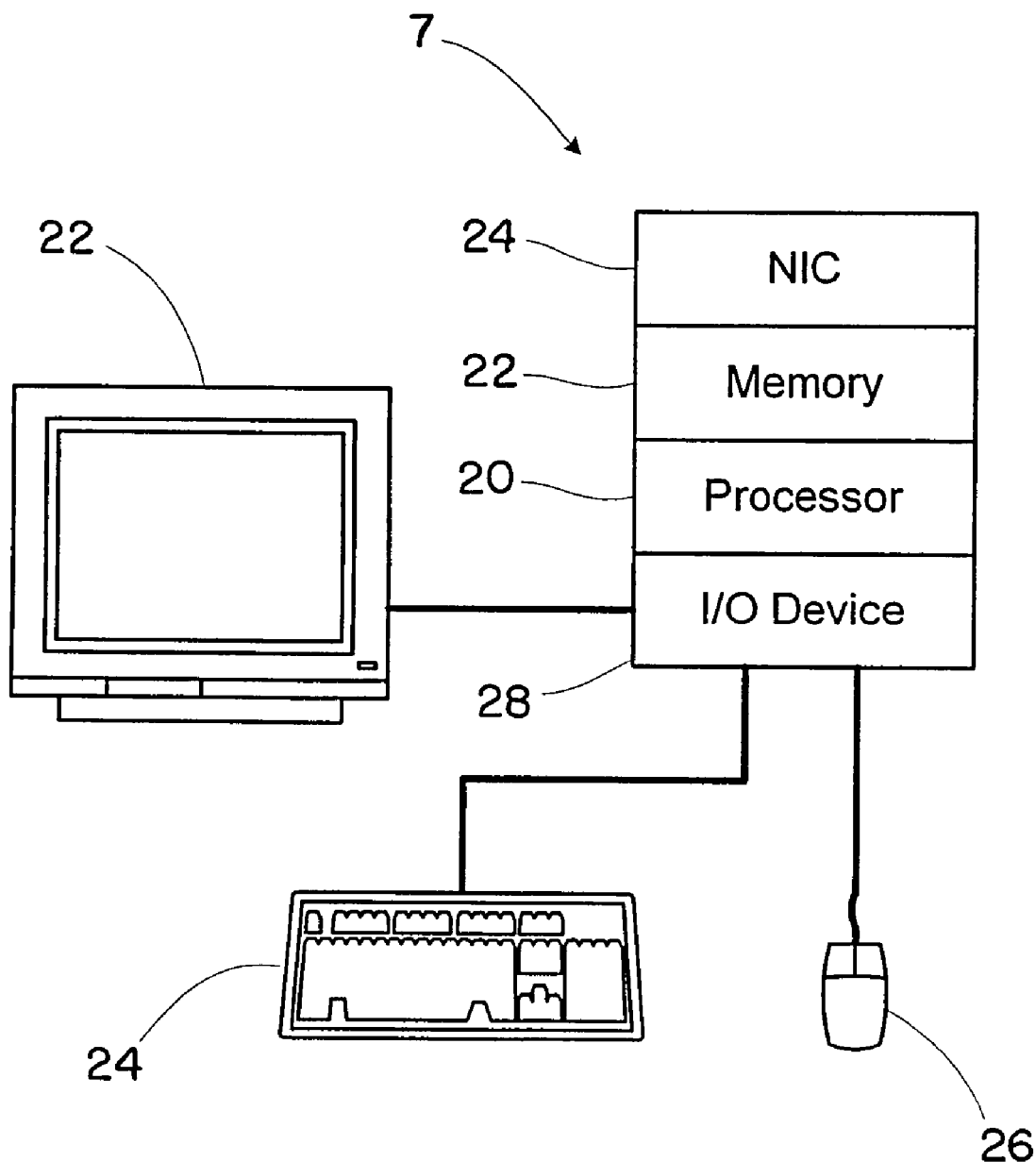
FIG. 4 is a block diagram of an exemplary computer system that can be used in the device of FIG. 3.

Moving now to FIG. 4 there is shown a block diagram of an exemplary computer 7 that may be used to implement one or more of the methods described herein. The computer 7 may include a display 22 for viewing system information, and a keyboard 24 and pointing device 26 for data entry, screen navigation, etc. A computer mouse or other device that points to or otherwise identifies a location, action, etc., e.g., by a point and click method or some other method, are examples of a pointing device 26. Alternatively, a touch screen (not shown) may be used in place of the keyboard 24 and pointing device 26. The display 22, keyboard 24 and mouse 26 communicate with a processor via an input/output device 28, such as a video card and/or serial port (e.g., a USB port or the like).

A processor 30, such as an AMD Athlon 64® processor or an Intel Pentium IV® processor, combined with a memory 32 execute programs to perform various functions, such as data entry, numerical calculations, screen display, system setup, etc. The memory 32 may comprise several devices, including volatile and non-volatile memory components. Accordingly, the memory 32 may include, for example, random access memory (RAM), read-only memory (ROM), hard disks, floppy disks, optical disks (e.g., CDs and DVDs), tapes, flash devices and/or other memory components, plus associated drives, players and/or readers for the memory devices. The processor 30 and the memory 32 are coupled using a local interface (not shown). The local interface may be, for example, a data bus with accompanying control bus, a network, or other subsystem.

The memory may form part of a storage medium for storing information, such as application data, screen information, programs, etc., part of which may be in the form of a database. The storage medium may be a hard drive, for example, or any other storage means that can retain data, including other magnetic and/or optical storage devices. A network interface card (NIC) 34 allows the computer 7 to communicate with other devices.

A person having ordinary skill in the art of computer programming and applications of programming for computer systems would be able in view of the description provided herein to program a computer system 7 to operate and to carry out the functions described herein. Accordingly, details as to the specific programming code have been omitted for the sake of brevity. Also, while software in the memory 32 or in some other memory of the computer and/or server may be used to allow the system to carry out the functions and features described herein in accordance with the preferred embodiment of the invention, such functions and features also could be carried out via dedicated hardware, firmware, software, or combinations thereof, without departing from the scope of the invention.

Computer program elements of the invention may be embodied in hardware and/or in software (including firmware, resident software, micro-code, etc.). The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for registering a non-patient-characteristic three-dimensional magnetic resonance data set (MR data set) to patient-characteristic data, comprising:
producing or providing a non-patient-characteristic three-dimensional generic model of a body or body part containing body structure data, said three-dimensional generic model correlated to the MR data set;
ascertaining or providing two-dimensional patient-characteristic detection data of a patient;
using a transformation protocol for data-linking the body structure data of the three-dimensional generic model to the two-dimensional patient-characteristic detection data to change or adapt the generic model of the body or body part based on the ascertained two-dimensional patient-characteristic detection data; and
using the transformation protocol to change or deform at least a part of the MR data set to generate a patient-characteristic three-dimensional MR data set that is registered to the fluoroscopic images.

2. The method according to claim 1, wherein the patient-characteristic data includes at least two fluoroscopic images of a patient.

3. The method according to claim 1, wherein producing or providing the non-patient-characteristic three-dimensional generic model of the body or body part includes producing or providing a surface model of the non-patient-characteristic three-dimensional generic model of a body or body part.

4. The method according to claim 1, wherein ascertaining or providing two-dimensional patient-characteristic detection data of the patient includes using at least two fluoroscopic images as the two-dimensional patient-characteristic detection data.

5. The method according to claim 1, wherein producing or providing the non-patient-characteristic three-dimensional generic model includes forming the generic model from at least one computer tomography reference data set (CT reference data set) and the at least one MR data set, said CT reference data set and MR data set being registered to each other.

6. The method according to claim 5, wherein producing the generic model includes forming from the at least one CT reference data set a three-dimensional CT reference data representation that is correlated with the generic model and/or forming from the at least one MR reference data set a three-dimensional MR reference data representation that is correlated with the generic model.

7. The method according to claim 5, wherein changing or adapting the generic model of the body or body part includes at least one of:
manually adapting the generic model with the aid of image representation assistance;
using an automatic image fusion method based on automatically identifying particular anatomical features; or
superimposing or fusing image data of the generic model with the computer tomographic (CT) or magnetic resonance (MR) data sets of the generic model.

8. The method according to claim 7, wherein manually adapting includes adapting by displacing points and landmarks or shifting, rotating, expanding or compressing the generic model on a screen output by via a user interface.

9. The method according to claim 7, wherein superimposing or fusing image data of the generic model includes using digitally reconstructed x-ray images as the image data of the generic model.

10. The method according to claim 1, wherein producing or providing the non-patient-characteristic three-dimensional generic model includes forming the generic model from a plurality of CT reference data sets and a plurality of corresponding MR data sets, said CT reference data set and MR data set being registered to each other.

11. The method according to claim 10, wherein producing the generic model includes forming from the at least one CT reference data set a three-dimensional CT reference data representation that is correlated with the generic model and/or forming from the at least one MR reference data set a three-dimensional MR reference data representation that is correlated with the generic model.

12. The method according to claim 1, further comprising using a fixed registration or transformation to register the adapted generic model to a corresponding patient-characteristic MR data set.

13. The method according to claim 1, wherein producing or providing a non-patient-characteristic three-dimensional generic model includes:
producing or providing a plurality of CT reference data sets;
selecting or ascertaining a CT reference data set as a CT main shape reference data set from the plurality of CT reference data sets;
producing or providing an MR main shape reference data set corresponding to the CT main shape reference data set;
registering the CT main shape reference data set to the MR main shape reference data set; and
generating the generic model from the other CT reference data sets of the plurality of CT reference data sets.

14. The method according to claim 13, further comprising applying the transformation protocol of the generic model to at least a part of the MR main shape reference data set that is registered to the CT main shape reference data set to generate the patient-characteristic three-dimensional MR data set.

15. The method according to claim 14, further comprising applying the transformation protocol to the part of the MR main shape reference data set that contains structures which are also displayed in the fluoroscopic images and/or the generic model.

16. The method according to claim 15, further comprising using a fixed registration of transformation to register the generated MR data set to a corresponding patient-characteristic MR data set.

17. The method according to claim 14, further comprising using a fixed registration of transformation to register the generated MR data set to a corresponding patient-characteristic MR data set.

18. The method according to claim 1, wherein using the transformation protocol for data-linking includes using a deformation and/or rotation protocol as the transformation protocol.

19. The method according to claim 1, wherein the generic model exhibits at least one of
- a typical and/or average body structure;
- a statistical model of a body structure;
- a plurality of body structures of the same type;
- a two-dimensional or three-dimensional data set of a body structure.

20. The method according to claim 19, wherein exhibiting a statistical model of the body structure includes a statistical model based on statistical evaluations of a plurality of image data sets.

21. The method according to claim 19, wherein exhibiting a two-dimensional or three-dimensional data set includes a geometric model.

22. A computer program embodied on a non-transitory machine readable medium for registering a non-patient-characteristic three-dimensional magnetic resonance data set (MR data set) to patient-characteristic data, comprising:
- code that produces or provides a non-patient-characteristic three-dimensional generic model of a body or body part containing body structure data, said three-dimensional generic model correlated to the MR data set;
- code that ascertains or provides two-dimensional patient-characteristic detection data of a patient;
- code that uses a transformation protocol for data-linking the body structure data of the three-dimensional generic model to the two-dimensional patient-characteristic detection data to change or adapt the generic model of the body or body part based on the ascertained two-dimensional patient-characteristic detection data; and
- code that uses the transformation protocol to change or deform at least a part of the MR data set to generate a patient-characteristic three-dimensional MR data set that is registered to the fluoroscopic images.

23. A device for registering a non-patient-characteristic three-dimensional magnetic resonance data set (MR data set) to patient-characteristic detection data, comprising:
- a data detection device for recording at least two fluoroscopic images containing two-dimensional patient-characteristic detection data;
- a navigation system for ascertaining a three-dimensional spatial position of the data detection device relative to a body or body part to be recorded; and
- a computational unit communicatively coupled to the navigation system, said computational unit configured to produce a three-dimensional generic model of a body or body part containing body structure data, wherein the three-dimensional generic model is at least correlated with MR data set;
- use a transformation protocol for data-linking the body structure data of the three-dimensional generic model to the two-dimensional patient-characteristic detection data to change or adapt the generic model of the body or body part, based on the ascertained two-dimensional patient-characteristic detection data; and
- use the transformation protocol to change or deform at least a part of the MR data set to generate a patient-characteristic three-dimensional MR data set that is registered to the fluoroscopic images.

24. The device according to claim 23, wherein the computational unit is configured to form the three-dimensional generic model from at least one computer tomography reference data set and the MR data set, the at least one computer tomography reference data set and the MR data set registered to each other.

\* \* \* \* \*